(12) United States Patent
Kasper et al.

(10) Patent No.: US 8,536,864 B2
(45) Date of Patent: Sep. 17, 2013

(54) METHOD FOR THE RELEASABLE FASTENING OF A COMPONENT TO AN APPARATUS AND CORRESPONDINGLY CONFIGURED FASTENING SYSTEM

(75) Inventors: Peter Kasper, Schweiz (CH); Robert Lindmayr, Birrwil (CH); Bernd Maciejewski, Markt Erlbach (DE)

(73) Assignee: Siemens Aktiengesellschaft, München (DE)

( * ) Notice: Subject to any disclaimer, the term of this patent is extended or adjusted under 35 U.S.C. 154(b) by 597 days.

(21) Appl. No.: 12/793,043

(22) Filed: Jun. 3, 2010

(65) Prior Publication Data
US 2010/0310304 A1    Dec. 9, 2010

(30) Foreign Application Priority Data
Jun. 4, 2009  (DE) .......................... 10 2009 023 858

(51) Int. Cl.
*G01V 3/00*    (2006.01)
(52) U.S. Cl.
USPC .......................................................... 324/300
(58) Field of Classification Search
USPC ..................... 324/300–322; 600/407–445
See application file for complete search history.

(56) References Cited

U.S. PATENT DOCUMENTS

| | | | | |
|---|---|---|---|---|
| 2,288,594 | A * | 7/1942 | Neracher et al. | 477/55 |
| 5,778,733 | A * | 7/1998 | Stringer | 74/527 |
| 6,223,873 | B1 * | 5/2001 | Ahnert et al. | 192/3.56 |
| 6,443,276 | B2 * | 9/2002 | Ahnert et al. | 192/3.56 |
| 6,658,979 | B1 * | 12/2003 | Frech et al. | 83/746 |
| 6,679,361 | B2 * | 1/2004 | Ahnert et al. | 192/3.56 |
| 2008/0081989 | A1 * | 4/2008 | Maciejewski | 600/410 |

FOREIGN PATENT DOCUMENTS

DE    102006046318 A1    4/2008

* cited by examiner

*Primary Examiner* — Brij Shrivastav

(57) ABSTRACT

A method and a fastening system for the releasable fastening of a component to an apparatus are described. Here the fastening system comprises a detent spring arranged on the apparatus, a detent pin with a groove arranged on the component and a Bowden cable arranged on the apparatus. If the component is fastened to the apparatus, the detent spring locks in the groove in a locking position. The Bowden cable is connected to the detent spring such that when pulling on the Bowden cable, the detent spring releases from the locking position in the groove, as a result of which the fastening of the component to the apparatus is released.

18 Claims, 12 Drawing Sheets

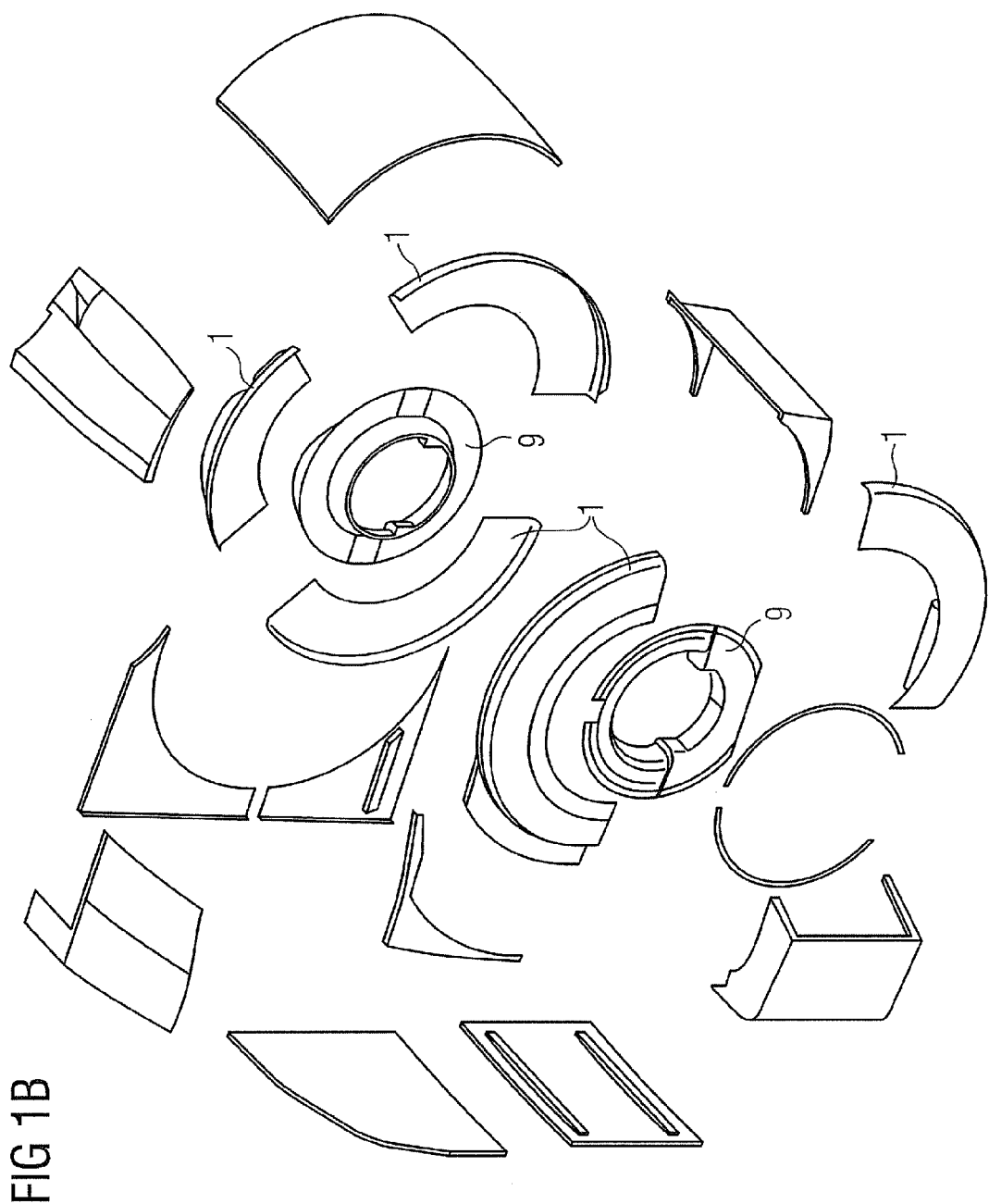

METHOD FOR THE RELEASABLE FASTENING OF A COMPONENT TO AN APPARATUS AND CORRESPONDINGLY CONFIGURED FASTENING SYSTEM

CROSS REFERENCE TO RELATED APPLICATIONS

This application claims priority of German application No. 10 2009 023 858.1 filed Jun. 4, 2009, which is incorporated by reference herein in its entirety.

FIELD OF THE INVENTION

The present invention relates to a method for fastening a component, for instance an inlet funnel, to an apparatus, for instance a system casing of an MR system, as well as a correspondingly configured fastening system.

BACKGROUND OF THE INVENTION

In the case of housing casings of MR systems, opposing requirements exist in terms of design, service and acoustics. On the one hand, the design should ensure that screw connections are as invisible as possible from the outside. On the other hand, the service requires all parts (inside the MR system) to be as easily accessible as possible, thereby almost inevitably requiring connecting elements which are easily visible from the outside. Furthermore, a vibration decoupling is advisable as a result of the acoustics, such that no direct screw connection with the base system of the magnet of the MR system is to be available. A screw connection of the inlet funnel of the MR system casing with the body coil ("HF pipe", "bore") generally results for instance in vibrations being transmitted from the body coil to the inlet funnel and this thus being induced to oscillate, thereby becoming negatively noticeable as noise in the manner of a loudspeaker.

SUMMARY OF THE INVENTION

It is thus the object of the present invention to improve the fastening of a casing in MR systems relative to the prior art.

This object is achieved in accordance with the invention by a fastening system a method for the releasable fastening of a component to an apparatus and a magnetic resonance system as claimed in the claims. The dependent claims define preferred and advantageous embodiments of the present invention.

Within the scope of the present invention, a fastening system is provided for the releasable fastening of a component to an apparatus. In this way, a detent spring fastened to the apparatus locks into a groove of a detent pin fastened to the component, with the detent spring being located in a locking position, if the component is fastened to the apparatus, i.e. if the detent spring is locked in the groove. Furthermore, a Bowden cable arranged on the apparatus is connected to the detent spring such that the detent spring can be released from the locking position in the groove by pulling on the Bowden cable, as a result of which the fastening of the component to the apparatus can also be released.

A corresponding arrangement of the detent spring, the detent pin and the Bowden cable enables the inventive fastening system to be configured such that no screw connections are visible from the outside and no decorative covers or other types of covers for screws are needed, as a result of which tool and part costs can be advantageously reduced compared with the prior art.

As it is only the detent spring that has to be locked in the groove of the detent pin, in order to attach the component to the apparatus, and only the Bowden cable that has to be actuated in order to release the component from the apparatus, the present invention has shorter disassembly and assembly times, by comparison with fastening systems as claimed in the prior art, which operate with a screw connection.

The fastening system also comprises a receptacle fastened to the apparatus, to which the detent spring is fastened. To fasten the component to the apparatus, the detent pin is inserted into the receptacle, with the detent spring in the locking position locking into the groove. To release the fastening of the component to the apparatus, the detent pin has to be guided out of the recess, the detent spring having being released (pulled) from the groove previously by actuating the Bowden cable, as a result of which the detent pin is no longer blocked by the detent spring and can be easily pulled out of the receptacle.

A first movement direction, in which the detent spring moves, is advantageously essentially at right angles to a second movement direction, in which the detent pin is moved into the receptacle when fastening the component to the apparatus and moved out of the receptacle when releasing the component from the apparatus. The second movement direction is also arranged here essentially in parallel to an axis of symmetry of the detent pin. The detent spring moves here in the first movement direction if the detent pin is guided into the recess or if the detent spring is moved by pulling on the Bowden cable. A movement direction is understood here to be both a forward direction and also a backward direction which is parallel to the forward direction.

In a preferred inventive embodiment of the fastening system, the receptacle has a bias spring fastened to the receptacle. When fastening the component to the apparatus, the detent pin is inserted into the receptacle counter to the bias spring, so that the bias spring is pretensioned after insertion of the detent pin into the receptacle. When releasing the fastening of the component from the apparatus, the detent pin is pushed out of the receptacle by the bias spring as a result of pretension (if the detent spring has previously been released from the locking position (from the groove) by way of the Bowden cable.

The bias spring almost automatically forces the detent pin out of the receptacle, provided it is no longer hindered by the detent spring and/or provided the Bowden cable is actuated. As a result, the component advantageously releases itself from the apparatus simply by actuating the Bowden cable, without a further manual operation by means of an operating person being needed herefor.

A direction of force, in which the bias spring is pretensioned upon insertion of the detent pin into the recess, is in particular essentially parallel here to the movement direction of the detent pin upon insertion into the receptacle or upon release from the receptacle. The direction of force is therefore essentially at right angles to the (previously described) first movement direction of the detent spring.

The detent pin advantageously has an upwardly tapered head, so that an insertion of the detent pin into the receptacle on the one hand and an insertion of the detent spring into the groove of the detent pin on the other hand is facilitated. This particularly facilitates the assembly, since large assembly tolerances are permitted, even if advantageously only small position tolerances are available.

Furthermore, the receptacle can comprise a stop, against which the detent spring strikes in the case of a pull by the Bowden cable, as a result of which a movement of the Bowden cable is limited when releasing the detent spring from the locking position in the groove, and the cable core of the Bowden cable (generally a non-magnetic wire or suchlike) is not overloaded (overstretched).

The detent spring can also further comprise a pretension, so that a tensile force applied to the detent spring by the Bowden cable has to release the detent spring from the locking position in the groove counter to the pretension.

In a preferred inventive embodiment of the fastening system, the fastening system has several of the previously described detent pints on the component and several of the previously described receptacles on the apparatus. Here the number of detent pins equates to the number of receptacles, with the detent pins being arranged on the component and the receptacles being arranged on the apparatus such that when fastening the component to the apparatus, each of the detent pins can be inserted into one of the receptacles. Furthermore, the fastening system according to this embodiment includes a releasing handle and a number of Bowden cables corresponding to the number of detent pins (or receptacles), said Bowden cables being actuated by way of the releasing handle. The Bowden cables are guided to the detent springs by the releasing handle such that each Bowden cable engages with one of the detent springs. When actuating the releasing handle, each detent spring is released from an engagement with the groove of its detent pin by way of the corresponding Bowden cable.

According to an inventive embodiment, the releasing handle has two detent points. With the first detent point, the releasing handle exerts almost no pull on the Bowden cables, so that the detent springs are locked into the grooves of the detent pins, if the component is attached to the apparatus. In the second detent point, which also retains the releasing handle, if the releasing handle is disengaged, the releasing handle exerts such a pull on the Bowden cable that all detent springs release out of the grooves and release the detent pins. On condition that the receptacles have no bias springs, the second locking point is used to release the engagement between the component and the apparatus, without releasing the component from the apparatus. To release the component from the apparatus, the component must be detached from the apparatus in this embodiment.

By each component having several detent pins and each apparatus having several receptacles, several detent pins can advantageously be arranged around an edge of the component, as a result of which the component can at the same time be fastened to the apparatus at several points.

Here the fastening system can include a power distributor and an additional Bowden cable. The additional Bowden cable is guided here to the force distributor by the unlocking handle, while the Bowden cables are guided from the force distributor to the assigned detent spring in each instance. Upon actuation of the unlocking handle, a force is transmitted from the unlocking handle, via the additional Bowden cable, to the force distributor and from the force distributor to the several Bowden cables and from there to the detent springs.

A length of the additional Bowden cable can be measured here such that the unlocking handle can be moved outside the apparatus in front of the component and can be actuated there. As a result, the component can be released by actuating the unlocking handle while the component can on the one hand be monitored by the operating person controlling the unlocking handle and if necessary, also be guided or moved manually.

The fastening system can also include an adjustable screw for each Bowden cable, with it being possible, with the aid of these adjustable screws, for a force transmission to be adjusted from the additional Bowden cable to the Bowden cable corresponding to the adjustable screw. If settling occurs on the section of a Bowden cable, this can herewith be balanced out.

The Bowden cables, the force distributor, the additional Bowden cable and the unlocking handle are preferably arranged here within the apparatus, in order not to interfere with the optical image of the apparatus (for instance a magnetic resonance system). E.g. by opening a service flap of the magnetic resonance system, the unlocking handle can then be removed from the apparatus in order to release the component from the apparatus.

To facilitate the fastening of the component to the apparatus, the component can include one or several guiding ridges, which are arranged on the periphery of the component. With the aid of the guide ridge or ridges, the component can be easily arranged in a position, in which the detent pins are inserted into the receptacles.

Furthermore, the fastening system can also include a securing leash, with which the component is attached to the apparatus so that when releasing the component from the apparatus (by actuating the unlocking handle), the component is prevented from falling out of the apparatus by means of a securing leash. In more precise terms, the length of the securing leash restricts the fall of the component, i.e. the length of the securing leash is generally defined such that the component does not fall onto the ground and/or onto the feet of the operating and/or service personnel, if it is released from the apparatus. To completely release the component from the apparatus, the securing leash must be manually released from the component or from the apparatus.

Within the scope of the present invention, a method for the releasable fastening of a component to an apparatus is also provided. When fastening the component to the apparatus, a detent spring arranged on the apparatus is engaged here with a groove of a detent pin arranged on the component such that the component is herewith fastened to the apparatus. When releasing the component from the apparatus, a Bowden cable is actuated, so that the engagement between the detent spring and the groove is released by actuating the Bowden cable.

The advantages of the inventive method essentially correspond to the advantages of the inventive fastening system, which are described in detail above, so there is no need for a repetition here.

The present invention is particularly suited to fastening a casing (component) to a magnetic resonance system (apparatus) or to fastening an inlet funnel (component) to a casing of a magnetic resonance system. The present invention is naturally not restricted to these preferred areas of application but can instead by used to fasten any components to any apparatuses.

BRIEF DESCRIPTION OF THE DRAWINGS

The present invention is described in detail below with the aid of preferred embodiments with reference to the figures, in which:

FIG. 1b shows an exploded view of the components of the casing in FIG. 1a.

DETAILED DESCRIPTION OF THE INVENTION

Figure 1A:
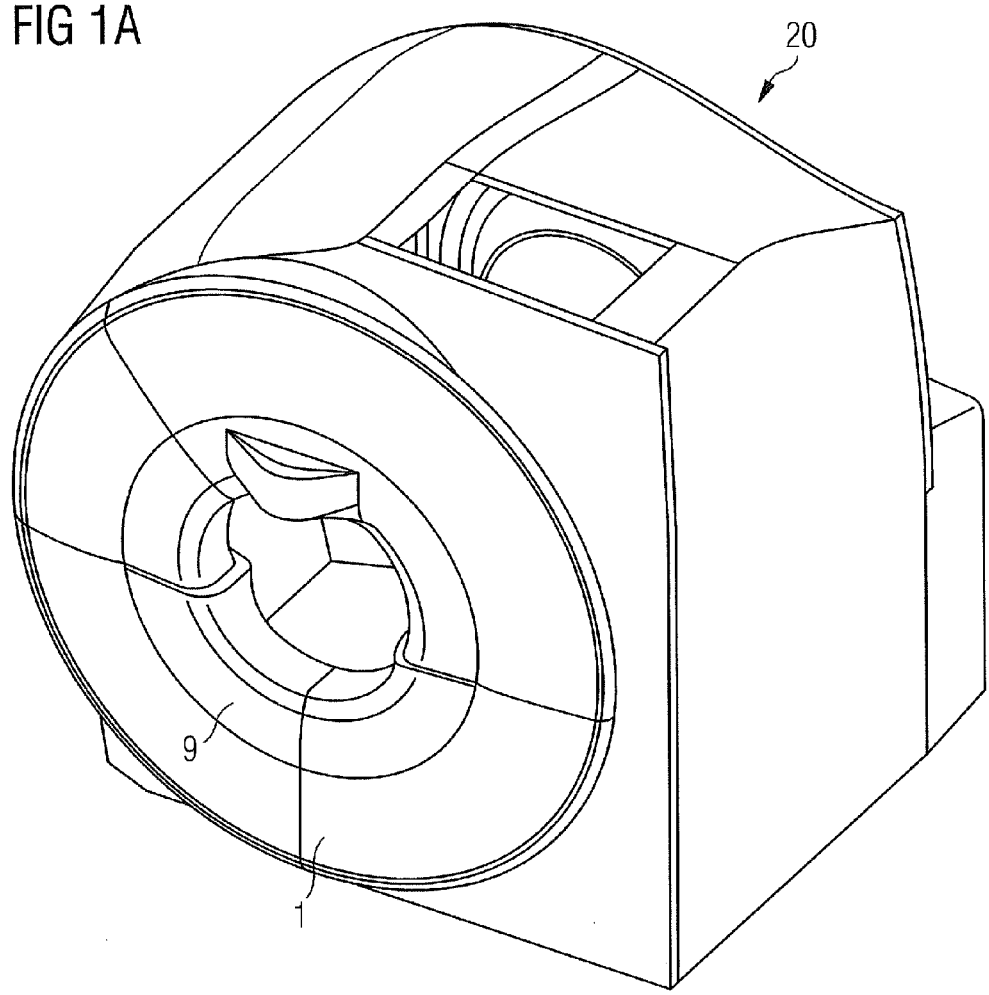
FIG. 1a represents an overview of a casing of a magnetic resonance system.

FIG. 1a shows an inventive casing 1 of a magnetic resonance system 20, to which an inlet funnel 9 is attached with the aid of the present invention.

FIG. 1b represents an exploded view of components of the casing of the magnetic resonance system.

Figure 2:
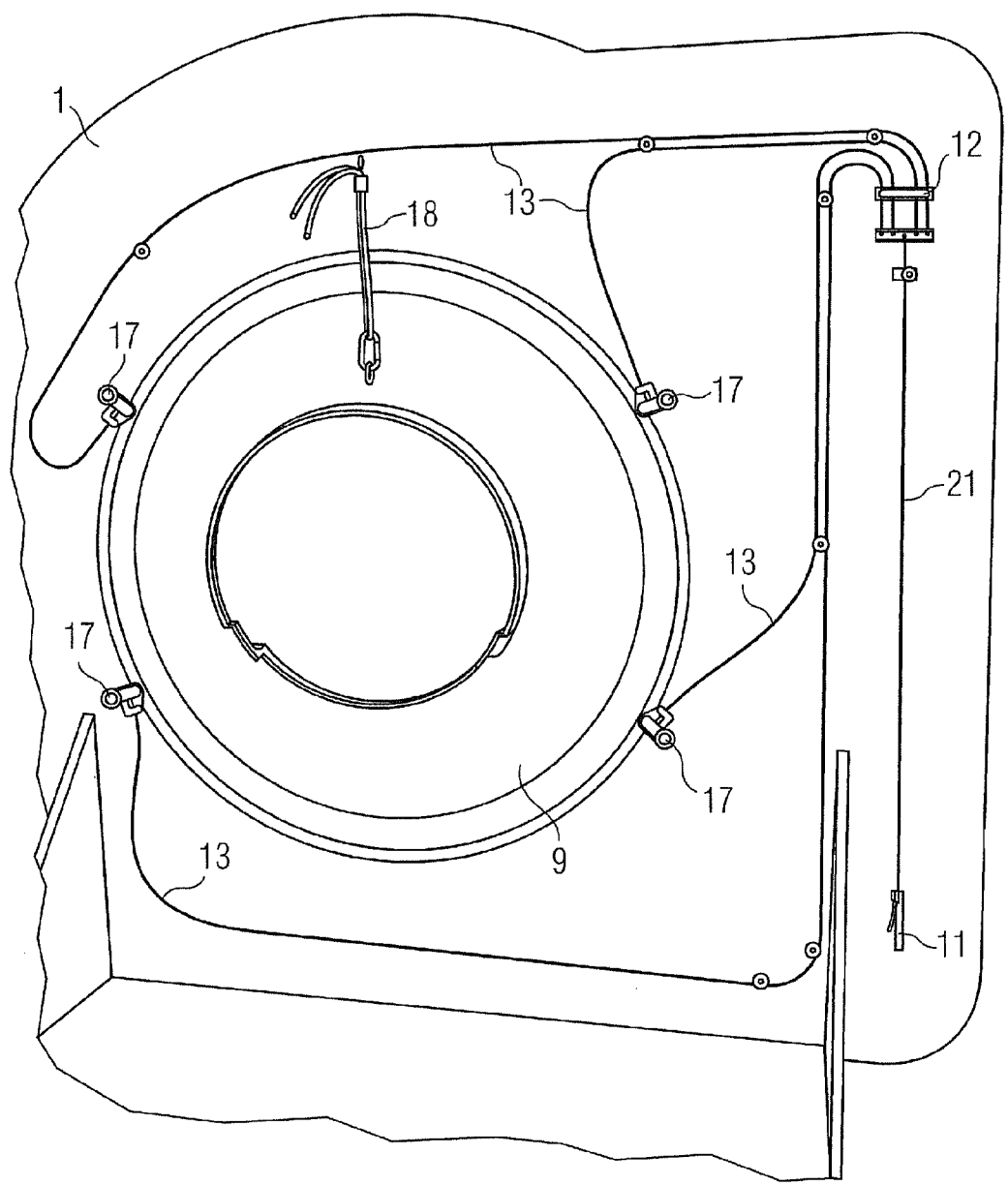
FIG. 2 represents the inlet funnel attached to the casing when viewed from inside the casing.

FIG. 2 shows an overall interior view of a rear and/or front casing of a magnetic resonance system with inventive rapid locking and unlocking system for fastening an inlet funnel 9 to the casing 1. An unlocking handle 11 and a force distributor 12 can be seen on the inside. Bowden cables 13 are guided from the force distributor 12 to four receptacles 17. A further Bowden cable 21 is located between the unlocking handle 11 and the force distributor 12. By actuating the unlocking handle 11, a force is guided to the force distributor 12 by way of the further Bowden cable 21, which then forwards this force to the Bowden cables 13, as a result of which the inlet funnel 9 is released, as is described again in detail below. Furthermore, a securing leash 18 is shown in FIG. 2, with which the inlet funnel 9 is attached to the casing 1, in order to prevent the inlet funnel 9 from falling onto the floor or from falling onto the feet of an operating person and/or damaging the casing 1 when the inlet funnel 9 is released from the casing 1.

Figure 3:
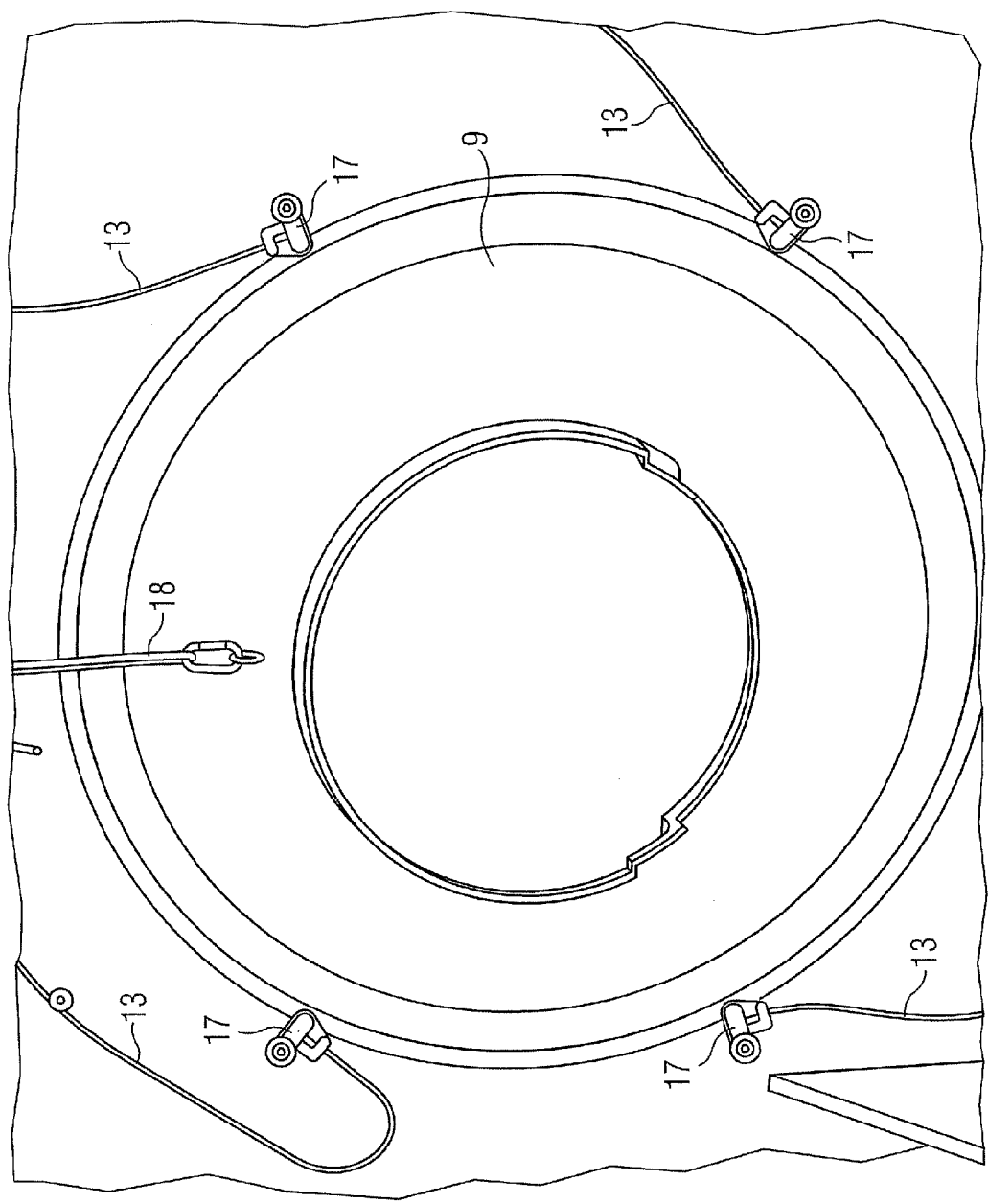
FIG. 3 shows a detailed representation of the inlet funnel attached to the casing when viewed from inside the casing.

A section of FIG. 2 is shown in detail in FIG. 3.

Figure 4:
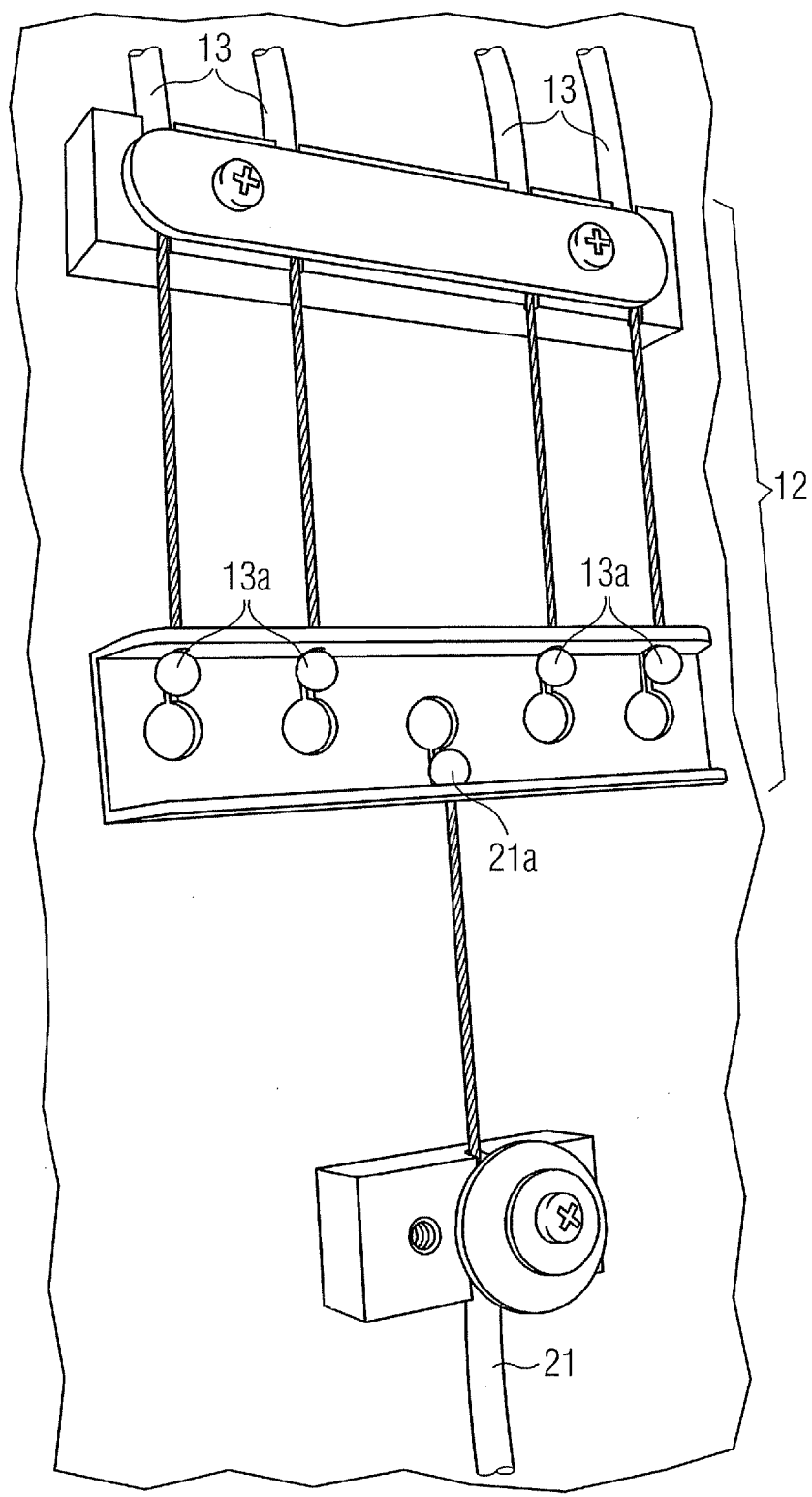
FIG. 4 represents an inventive force distributor.

FIG. 4 shows the force distributor 12 in detail. When actuating the unlocking handle 11, a force is applied to the force distributor 12 by way of the further Bowden cable 21 by means of a sphere 21a. The force distributor 12 then in turn forwards this force via a sphere 13a to the four Bowden cables 13 in each instance. Each Bowden cable 13 can therefore be mounted in the force distributor 12 or released from the force distributor 12 by means of its sphere 13a.

Figure 5:
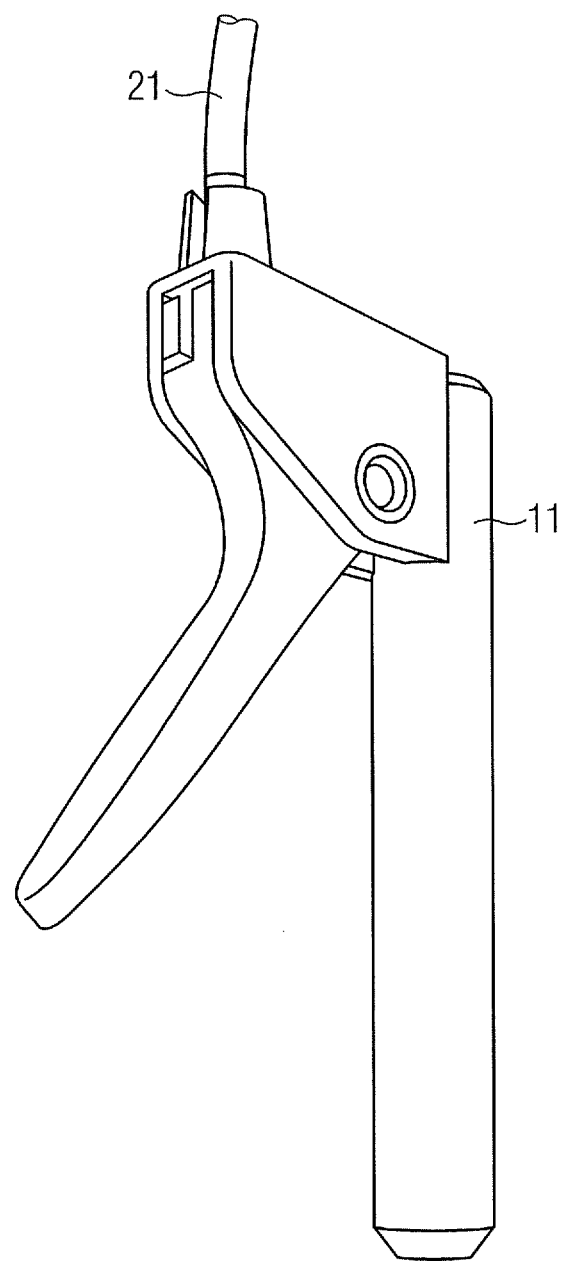
FIG. 5 represents an inventive unlocking handle.

FIG. 5 represents an unlocking handle 11 at close range. This unlocking handle 11 is normally arranged inside the casing 1 and/or magnetic resonance system 20. The unlocking handle 11 can however be guided out of the casing 1 in order to release the inlet funnel 9 from the casing 1, if the length of the further Bowden cable 21 connected to the unlocking handle 11 enables this.

Figure 6:
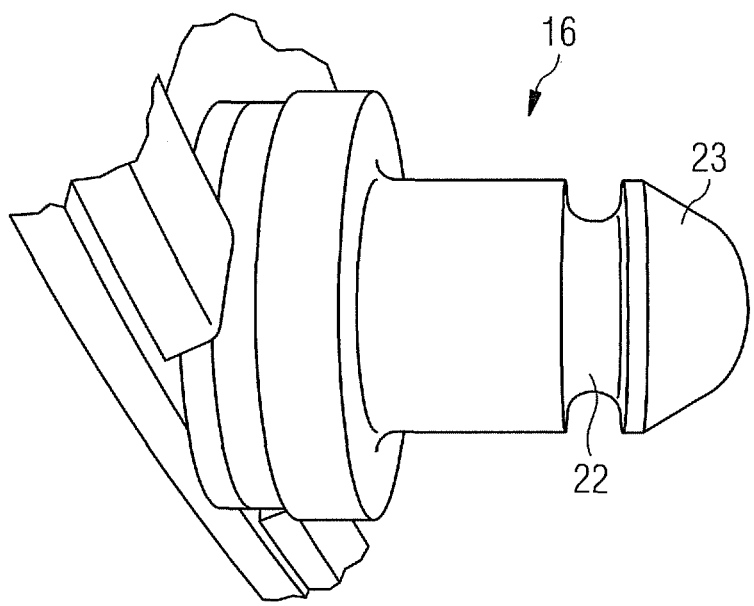
FIG. 6 represents an inventive detent pin.

FIG. 6 shows a detent pin 16 at close range. An upwardly tapered head 23 of the detent pin 16 can be seen, with the aid of which an insertion of the detent pin 16 into a receptacle 17 and thus a locking of a detent pin 16 in a groove 22 of the detent pin 16 is facilitated.

Figure 7:
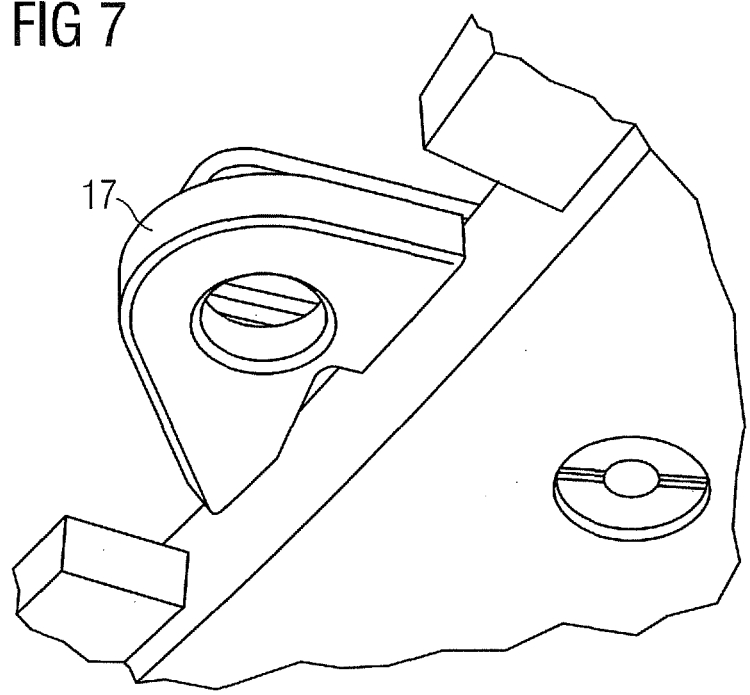
FIG. 7 represents an inventive receptacle.

FIG. 7 shows a side view of a receptacle 17, from which the detent pin 16 is inserted into the receptacle 17 in order to fasten the inlet funnel 9 to the casing 1.

Figure 8:
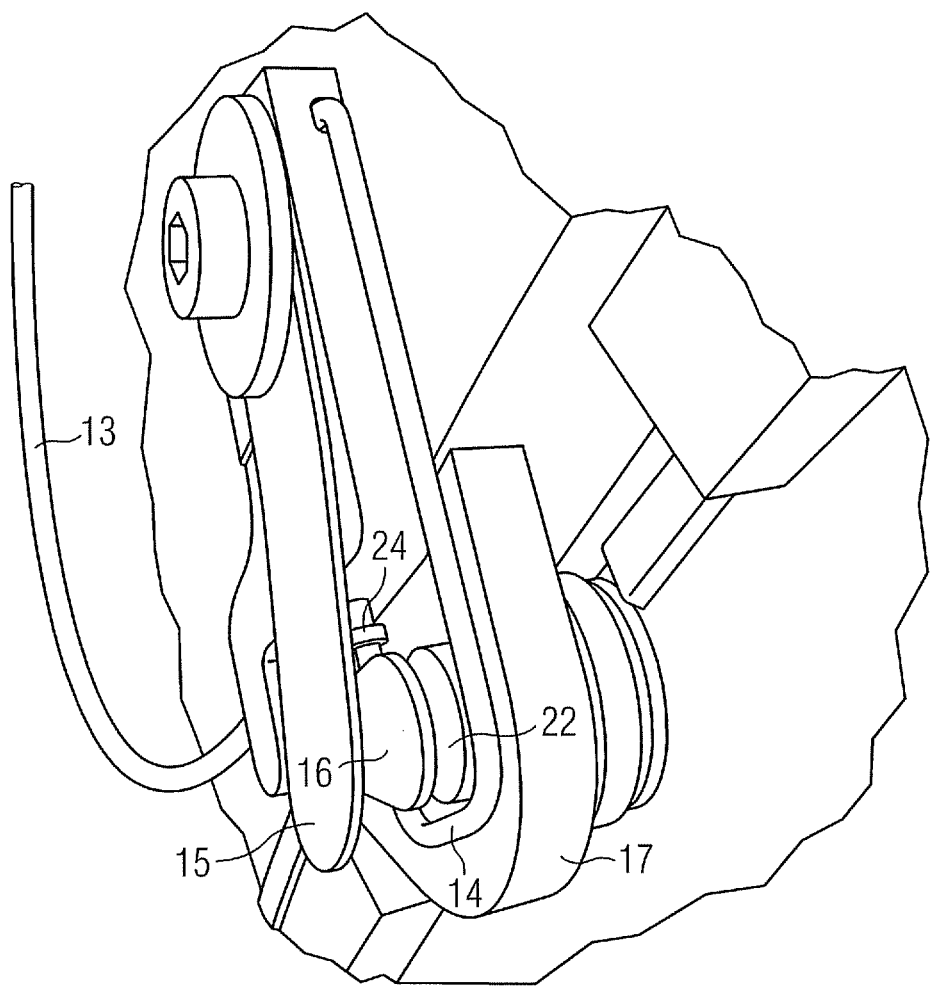
FIG. 8 is a side representation of an inventive receptacle with a detent pin locked therein.

FIG. 8 shows a receptacle 17 obliquely from the side, with a detent pin 16 locked to the detent spring or a round wire spring 14 of the receptacle 17 being located in the receptacle 17. It is apparent that the detent pin 16 engages with the round wire spring 14, although a force is exerted onto the detent pin by means of a leaf spring 15 of the receptacle 17. It is only when the Bowden cable 13 which is fastened to the round wire spring 14 by way of an eyelet 24 is actuated that the round wire spring 14 is pulled out of the groove 22, so that the engagement between the round wire spring 14 and the detent pin 16 releases, as a result of which the detent pin 16 is moved out of the receptacle 17 by means of the pretensioned leaf spring 15.

Figure 9:
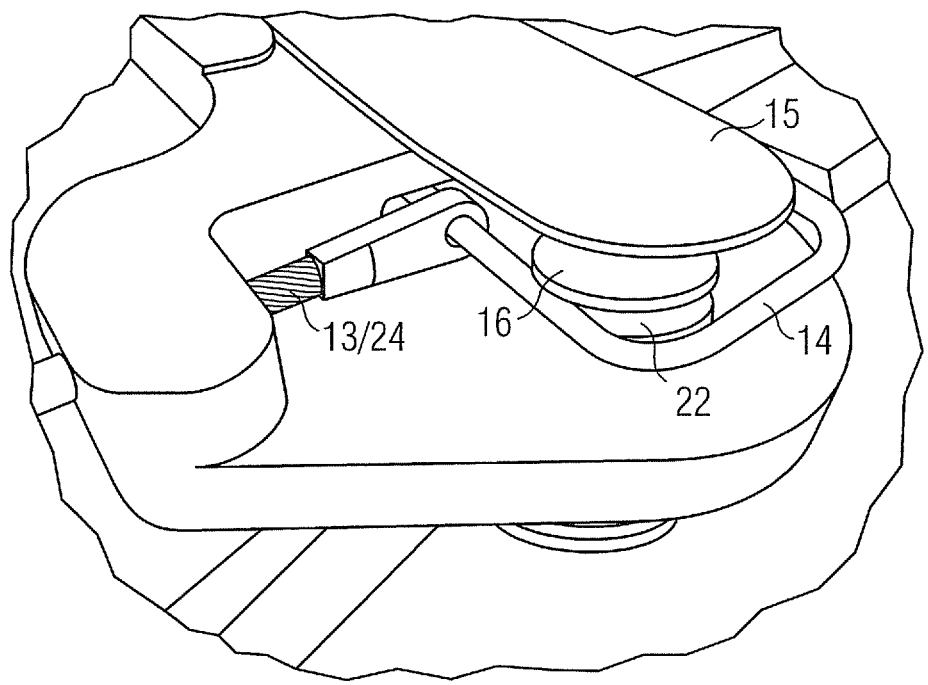
FIG. 9 represents a top view of an inventive receptacle with a detent pin locked therein.

FIG. 9 shows an oblique top view of the receptacle 17 with the detent pin 16 of FIG. 8 which is locked therein. It is clearer in FIG. 9 (than in FIG. 8) that pulling on the Bowden cable 13 to the left (in FIG. 9) releases the catch mechanism between the detent pin 22 and the round wire spring 22, since the round wire spring 14 is pulled to the left out of the groove 22 by means of the pull.

Figure 10:
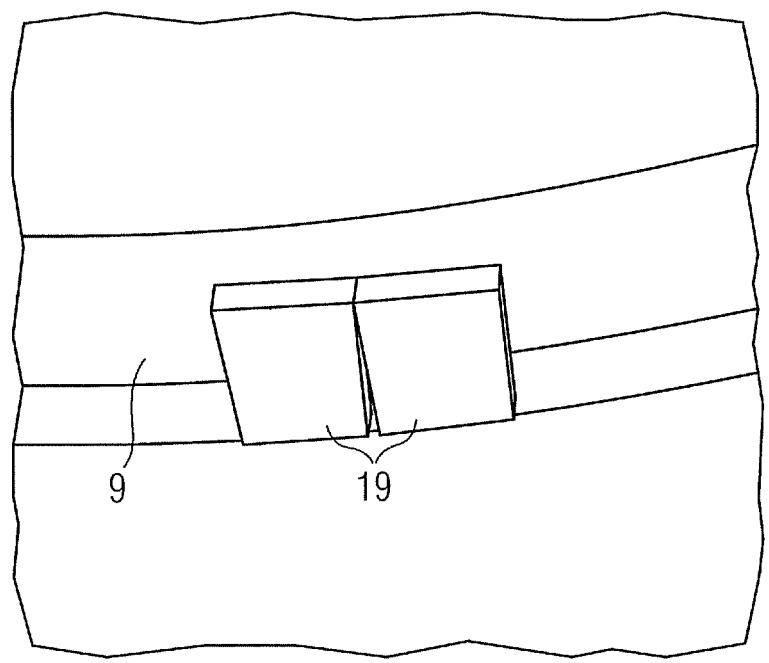
FIG. 10 represents inventive guiding ridges.

FIG. 10 shows two guiding ridges 19, which are attached to the bottom of the inlet funnel 9 (on the lower edge). With the aid of these guiding ridges 19, the inlet funnel 9 can be set up so as fasten to the casing 1, as a result of which an engagement of the four detent pins 16 into the receptacles 17 is facilitated. Instead of the two guiding ridges 19 shown, only one guiding ridge or more than two guiding ridges can naturally also be present. Furthermore, the distance between the guiding ridges 19 can be selected to be greater than that shown in FIG. 10.

Figure 11:
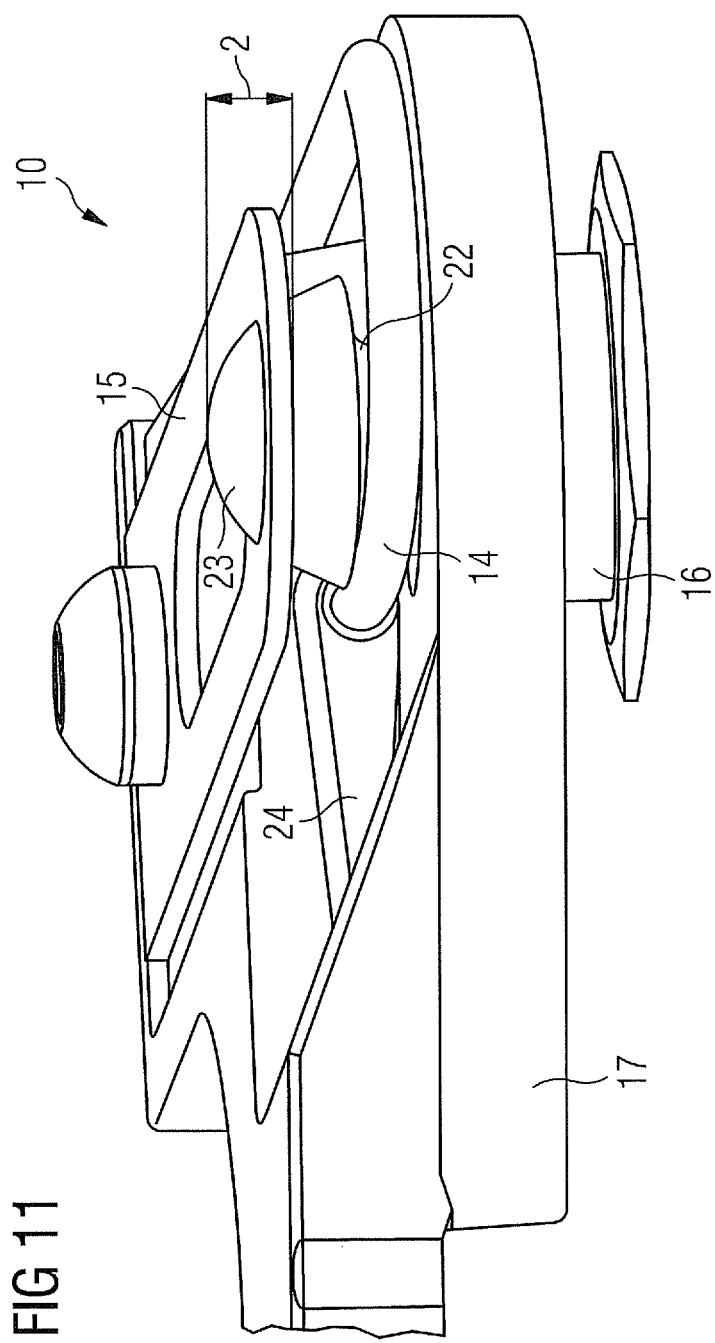
FIG. 11 represents a design sketch of an inventive fastening system.

FIG. 11 shows a design sketch of an inventive fastening system 10 in the zero position. In the zero position, all components (e.g. the leaf spring 15) are shown without a pretensioning, as a result of which the head 23 of the detent pin is shown as almost passing through the leaf spring 15. The receptacle or the bearing 17 (counter bearing for the Bowden cable 13) is fastened to the actual front casing 1 (not visible in FIG. 11) from the inside, so that the receptacle 17 is not visible from the outside. A fastening of the receptacle 17 to the casing 1 is possible by means of adhesion or screwing for instance. The centering or detent pin 16 is fastened to the inlet funnel 9 from the rear, so that it is likewise not visible from the outside if the inlet funnel 9 is attached to the casing 1.

In the embodiment shown in FIG. 11, the leaf spring 15 has a pretension 2 of 3 mm. Since the components illustrated in FIG. 11 are shown to scale, the dimensions of the other components shown in FIG. 11 result accordingly by way of the pretension 2 of 3 mm. In the embodiment shown in FIG. 11, the round wire spring 14 has no pretension. However, a pretension of 0.5 mm for instance is possible if the detent pin 16 is engaged with the round wire spring 14.

Figure 12:
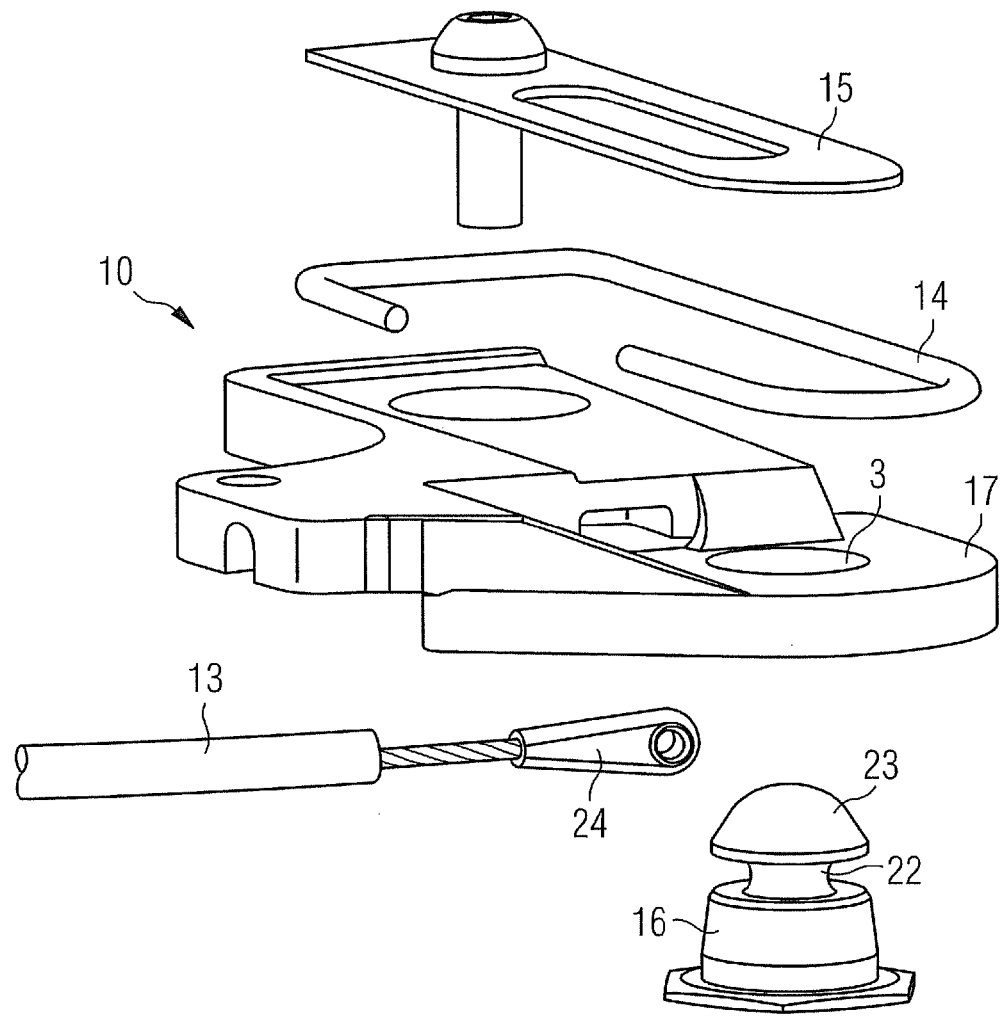
FIG. 12 represents a design sketch of the individual components of an inventive fastening system.

FIG. 12 shows the fastening system 10 shown in FIG. 11 as a three-dimensional exploded view.

Figure 13:
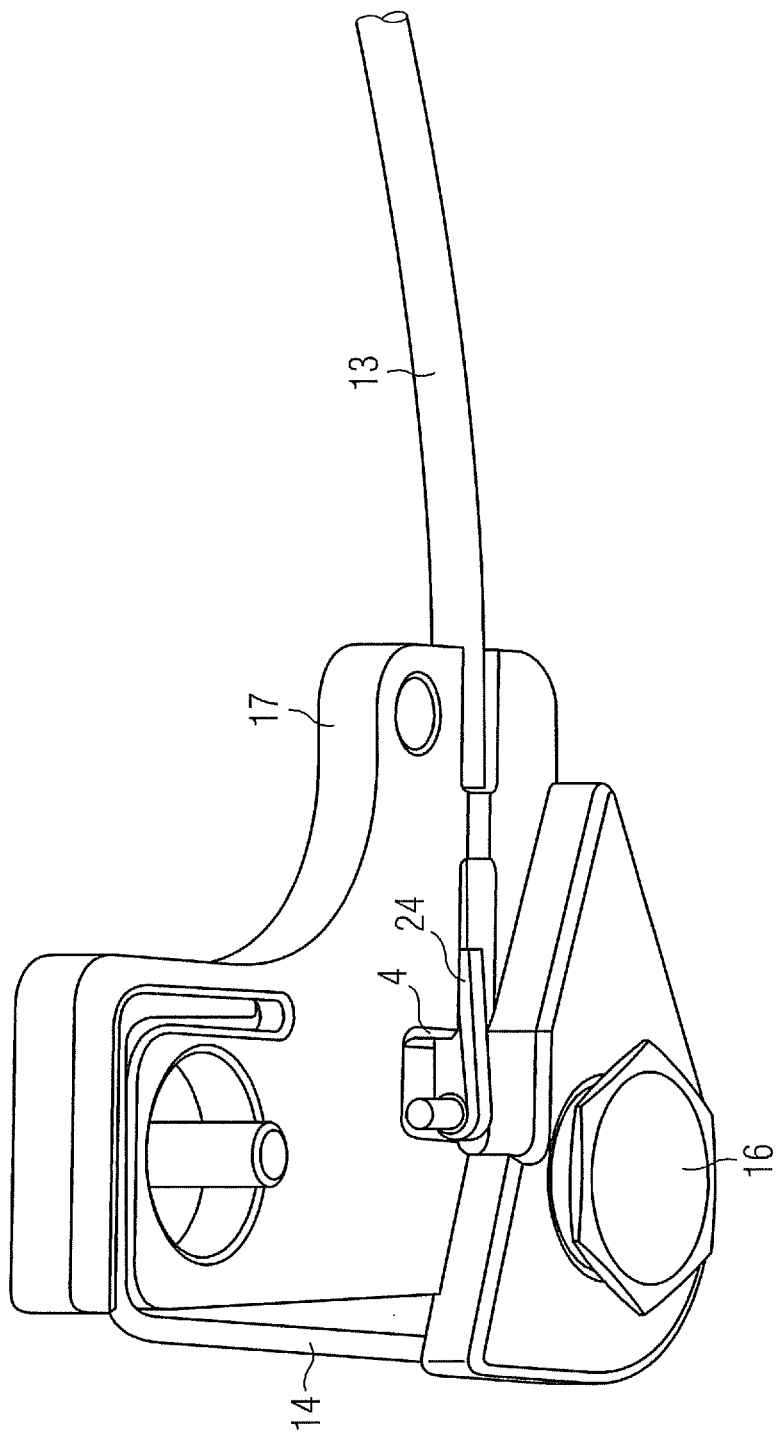
FIG. 13 represents a design sketch of an inventive fastening system from below.

FIG. 13 shows the inventive fastening system 10 shown in FIGS. 11 and 12 from below. A stop of the receptacle 17 is shown with reference character 4. A movement of the round wire spring 15 as a result of the pull by the Bowden cable 13 is advantageously restricted by means of this stop 4. This herewith prevents the round wire spring 14 or the receptacle 17 from being destroyed (overstretched) by way of the excessively large tensile force applied to the Bowden cable 13.

The fastening and release of the inlet funnel 9 by means of the inventive snap-fit and securing mechanism 10 comprising the unlocking system to (from) the casing 1 is described again below with the aid of FIGS. 11 to 13.

The detent pins 16 or more precisely the heads 23 of the detent pins 16 are inserted into a respective hole 3 of the corresponding receptacle 17 in order to fasten the inlet funnel 9 to the casing 1 (i.e. the centering and detent pins 16 are centered in the receptacle 17). The tapering head 23 herewith pushes the round wire spring 14 to the side on the one hand and pushes the leaf spring 15 upwards on the other hand. The round wire spring 14 engages in the guide groove 22 of the detent pin 16 if the detent pin 16 is inserted correspondingly far into the receptacle 17. If the round wire spring 14 engages in the groove 22, the detent pin 16 is locked to the receptacle 17 and can no longer be pulled out of the receptacle 17 (without actuating the Bowden cable 12).

To release the inlet funnel 9 from the casing 1, a service flap (not shown) of the casing 1 is opened, behind which is arranged the unlocking handle 11. The unlocking handle 11 is completely removed together with the additional Bowden cable 21 and guided and actuated upstream of the inlet funnel 9. By actuating the unlocking handle 11, the force, with which the unlocking handle 11 is actuated, is guided to the force distributor 12 by way of the additional Bowden cable 21. By means of the force distributor 12, this force is distributed equally onto the Bowden cables 13 and is guided to the receptacles 17 and/or more precisely to the round wire springs 14. The round wire springs 14 are pulled out of the respective guide groove 22 by actuating the unlocking handle 11, i.e. the round wire springs 14 snap out of the respective guide groove 22. As a result of the pretension 2, which prevails in the leaf springs 15, the locking pins 16 are pushed out of their mounting and/or receptacle 17, as a result of which the inlet funnel 9 releases from the casing 1. The securing leash 18 prevents the inlet funnel 9 from falling onto the floor or onto the feet of an operating person.

The afore-described service flap of the magnetic resonance system 20 has screws, by way of which the service flap is opened and/or closed. As it is not only the unlocking handle but instead the electronics system of the magnetic resonance system 20 that can be accessed by way of the service flap, there is a rule in most countries that the service flap is only to be opened using a tool (e.g. a screwdriver).

As, in the embodiment shown, the inlet funnel 9 is only attached to the casing 1, no vibrations are transmitted from the body coil or from the magnetic endspinning to the inlet funnel 9 and thus to the front or rear casing of the magnetic resonance system.

The invention claimed is:

1. A fastening system for releasing a component from an apparatus, comprising:
   a detent pin comprising a groove arranged on the component;
   a receptacle comprising a detent spring fastened to the apparatus, wherein the detent pin is inserted into the receptacle and is locked to the detent spring in a locking position in the groove for fastening the component to the apparatus and is guided out of the receptacle for releasing the component from the apparatus; and
   a Bowden cable arranged on the apparatus and connected to the detent spring that releases the detent spring in the groove from the locking position by pulling on the Bowden cable for releasing the component from the apparatus.

2. The fastening system as claimed in claim 1, wherein a first movement direction of the detent spring is essentially at a right angle to a second movement direction of the detent pin.

3. The fastening system as claimed in claim 1, wherein the receptacle comprises a bias spring fastened to the receptacle and the detent pin is inserted into the receptacle counter to the bias spring for fastening the component to the apparatus and is forced out of the receptacle by the bias spring when releasing the component from the apparatus.

4. The fastening system as claimed in claim 3, wherein a movement direction of the detent spring is essentially at a right angle to a force direction in which the bias spring is pretensioned.

5. The fastening system as claimed in claim 1, wherein the detent pin has a tapering in a direction of the receptacle in order to facilitate insertion of the detent pin into the receptacle.

6. The fastening system as claimed in claim 1, wherein the receptacle has a stop for limiting a movement of the Bowden cable when releasing the detent spring out of the locking position in the groove.

7. The fastening system as claimed in claim 1, wherein the detent spring has a pretension in the locking position and releases from the locking position in the groove counter to the pretension when pulling on the Bowden cable.

8. The fastening system as claimed in claim 1, further comprising:
   a plurality of detent pins arranged on the component with grooves,
   a plurality of detent spring arranged on the apparatus,
   a plurality of Bowden cables arranged on the apparatus and connected to the detent springs, and
   an unlocking handle that actuates the Bowden cables and guides the Bowden cables to the detent springs for releasing the detent springs in the grooves.

9. The fastening system as claimed in claim 8, further comprising:
   a force distributor,
   an additional Bowden cable that is guided by the unlocking handle to the force distributor,
   wherein the Bowden cables are guided by the force distributor to the detent springs by a force transmitted from the additional Bowden cable to the Bowden cables for releasing the detent springs in the grooves when actuating the unlocking handle.

10. The fastening system as claimed in claim 9, wherein the additional Bowden cable comprises a length so that the unlocking handle for releasing the component from the apparatus can be moved outside the apparatus.

11. The fastening system as claimed in claim 9, wherein the Bowden cables comprise adjustable screws for adjusting the force transmission from the additional Bowden cable to the Bowden cables.

12. The fastening system as claimed in claim 1, wherein the component comprises at least one guiding ridge on a periphery of the component in order to facilitate the fastening of the component to the apparatus.

13. The fastening system as claimed in claim 1, further comprising a securing leash for connecting the component to the apparatus, wherein the securing leash comprises a length for restricting a fall of the component and can be manually released from the component and/or from the apparatus.

14. The fastening system as claimed in claim 1, wherein the apparatus is a magnetic resonance system and the component is a casing of the magnetic resonance system.

15. The fastening system as claimed in claim 1, wherein the apparatus is a casing of a magnetic resonance system and the component is an inlet funnel of the magnetic resonance system.

16. A method for releasing a component from an apparatus, comprising:
   arranging a detent pin comprising a groove on the component;
   fastening a receptacle comprising a detent spring to the apparatus;
   inserting the detent pin into the receptacle locked to the detent spring in a locking position in the groove for fastening the component to the apparatus and guiding out of the receptacle for releasing the component from the apparatus;

arranging a Bowden cable on the apparatus and connecting to the detent spring; and actuating the Bowden cable for releasing the detent spring from the locking position in the groove.

17. A magnetic resonance system, comprising:

a detent pin comprising a groove arranged on a component of the magnetic resonance system;

a receptacle comprising a detent spring fastened to the apparatus, wherein the detent pin is inserted into the receptacle and is locked to the detent spring in a locking position in the groove for fastening the component to the apparatus and is guided out of the receptacle for releasing the component from the apparatus; and a Bowden cable arranged on the magnetic resonance system and connected to the detent spring that releases the detent spring in the groove from the locking position by pulling on the Bowden cable for releasing the component from the magnetic resonance system.

18. The magnetic resonance system as claimed in claim 17, the component is a casing of the magnetic resonance system.

* * * * *